(12) United States Patent
Bronich et al.

(10) Patent No.: US 7,332,527 B2
(45) Date of Patent: Feb. 19, 2008

(54) CROSS-LINKED IONIC CORE MICELLES

(75) Inventors: Tatiana K. Bronich, Omaha, NE (US); Alexander V. Kabanov, Omaha, NE (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 653 days.

(21) Appl. No.: 10/440,221

(22) Filed: May 16, 2003

(65) Prior Publication Data

US 2004/0228823 A1 Nov. 18, 2004

(51) Int. Cl.
*A61K 47/00* (2006.01)
(52) U.S. Cl. .................. 514/772.1; 424/400; 424/490; 514/772.3
(58) Field of Classification Search ...................... None
See application file for complete search history.

(56) References Cited

U.S. PATENT DOCUMENTS

| | | | |
|---|---|---|---|
| 4,808,314 A * | 2/1989 | Karplus et al. ............. | 210/638 |
| 6,333,051 B1 | 12/2001 | Kabanov et al. | |
| 6,383,500 B1 | 5/2002 | Wooley et al. | |

FOREIGN PATENT DOCUMENTS

| WO | WO 98/56334 | 12/1998 |
|---|---|---|
| WO | WO 98/56348 | 12/1998 |

OTHER PUBLICATIONS

Kabanov, Alexander V. et al. "Soluble Stoichiometric Complexes from Poly(N-ethyl-4-vinylpyridinium) Cations and Poly(ethylene oxide)-block-polymethacrylate Anions." *Macromolecules* 1996, 29: 6797-6802.
Bronich, Tatiana K. et al. "Soluble Complexes from Poly(ethylene oxide)-block-polymethacrylate Anions and N-Alkylpyridinium Cations." *Macromolecules* 1997, 30: 3519-3525.
Kabanov, Alexander V. et al. "Spontaneous Formation of Vesicles from Complexes of Block Ionomers and Surfactants." *J. Am. Chem. Soc.* 1998, 120: 9941-9942.
Vinogradov, Serguei V. et al. "Self-Assembly of Polyamine-Poly(ethylene glycol) Copolymers with Phosphorothioate Oligonucleotides." *Bioconjugate Chem.* 1998, 9: 805-812.
Bronich, Tatiana K. et al. "Self-Assembly in Mixtures of Poly(ethylene oxide)-graft-Poly(ethyleneimine) and Alkyl Sulfates." *Langmuir* 1998, 14: 6101-6106.
Bronich, Tatiana K. et al. "Novel drug delivery systems based on the complexes of block ionomers and surfactants of opposite charge." *Colloids and Surfaces B: Biointerfaces* 1999, 16: 243-251.

Bronich, Tatiana K. et al. "Effects of Block Length and Structure of Surfactant on Self-Assembly and Solution Behavior of Block Ionomer Complexes." *Langmuir* 2000, 16: 481-489.
Bronich, Tatiana K. et al. "Steric Stabilization of Negatively Charge Liposomes by Cationic Graft Copolymer." *Langmuir* 2000, 16: 4877-4881.
Bronich, Tatiana K. et al. "Interaction of Nanosized Copolymer Networks with Oppositely Charged Amphiphilic Molecules." *Nano Letters* 2001, 1, No. 10: 535-540.
Vinogradov, Serguei V. et al. "Nanosized cationic hydrogels for drug delivry: preparation, properties and interactions with cells." *Advanced Drug Delivery Reviews* 2002, 54: 135-147.
Lysenko, Eugene A. et al. "Block Ionomer Complexes with Polystyrene Core-Forming Block in Selective Solvents of Various Polarities. 2. Solution Behavior and Self-Assembly in Nonpolar Solvents." *Macromolecules* 2002, 35: 6344-6350.
Bronich, Tatiana K. et al. "Synthesis of Vesicles on Polymer Template." *J. Am. Chem. Soc.* 2002, 124: 11872-11873.
Han, Man Jung et al. "Synthesis, Characterization, and Biological Activity of Polyanion-cis-diammineplatinum(II) Complexes as Antitumor Agents." *Journal of Bioactive and Compatible Polymers* 1992, 7: 358-369.
Bogdanov, A. A. et al. "An Adduct of cis-Diamminedichlorophatinum(II) and Poly(ethylene glycol)poly(L-lysine)-Succinate: Synthesis and Cytotoxic Properties." *Bioconjugate Chem.* 1996, 7: 144-149.
Bogdanov, A. A. et al. "A Long-Circulating Co-Polymer in "Passive Targeting" to Solid Tumors." *Journal of Drug Targeting* 1997, 4, No. 5: 321-330.
Yokoyama, Masayuki et al. "Introduction of cisplatin into polymeric micelle." *Journal of Controlled Release* 1996, 39: 351-356.
Nishiyama, Nobuhiro et al. "Preparation and Characterization of Self-Assembled Polymer-Metal Complex Micelle from cis-Dichlorodiammineplatinum(II) and Poly(ethylene glycol)-Poly($\alpha\beta$-aspartic acid) Block Copolymer in an Aqueous Medium." *Langmuir* 1999, 15: 377-383.
Nishiyama, Nobuhiro et al. "Preparation and characterization of size-controlled polymeric micelle containing cis-dichlorodiammineplatinum(II) in the core." *Journal of Controlled Release* 2001, 74: 83-94.
Mizumura, Yasuo et al. "Cisplatin-incorporated Polymeric Micelles Eliminate Nephrotoxicity, While Maintaining Antitumor Activity." *Jpn. J. Cancer Res.* 2001, 92: 328-336.

* cited by examiner

Primary Examiner—Michael P. Woodward
Assistant Examiner—Eric E. Silverman
(74) Attorney, Agent, or Firm—Patterson & Sheridan, L.L.P.

(57) ABSTRACT

The present invention provides polymer micelles with cross-linked ionic cores as delivery vehicles for therapeutics, diagnostics, nucleic acids, proteins, small molecules and the like. The present invention provides additionally methods of synthesis and uses for such micelles.

27 Claims, 3 Drawing Sheets

CROSS-LINKED IONIC CORE MICELLES

STATEMENT REGARDING FEDERALLY SPONSORED RESEARCH

This invention was made with Government support. The Government has certain rights in this invention.

BACKGROUND OF THE INVENTION

Amphiphilic block copolymers, having a large solubility difference between hydrophilic and hydrophobic blocks, are known to assemble in aqueous solutions into polymer micelles of nanoscale size (see, e.g., Moffitt, M., et al. *Acc. Chem. Res.* 29: 95-102 (1996)). Such micelles have a fairly narrow size distribution and are characterized by their unique core-shell architecture, where hydrophobic blocks are segregated from the aqueous exterior to form an inner core surrounded by a shell of hydrophilic polymer chains. A micelle is thermodynamically stable relative to disassembly into single chains as long as the concentration of the block copolymer exceeds the critical micelle concentration (CMC).

Aggregation number, size, and shell architecture parameters of polymer micelles are essential characteristics for determining whether micelles will be useful in pharmaceutical applications. In general, the hydrophobic micelle core serves as a microenvironment for the incorporation of various therapeutic or diagnostic reagents while the hydrophilic shell or exterior stabilizes the micelles in aqueous dispersion. Poly(ethylene oxide) (PEO) is frequently used as the hydrophilic block of micelle-forming copolymers, since this polymer is known to be highly hydrated, soluble, non-toxic, non-immunogenic, and is able to serve as an efficient steric protector for various microparticulates such as liposomes, nanoparticles, or nanocapsules in biological media (see, e.g., Kwon, G. S. and Kataoka, K., *Adv. Drug Deliv. Rev.* 16: 295-309 (1995); and Tobio, M., et al. *Pharm. Res.* 15: 270-275 (1998)). In particular, PEO chains prevent particle opsonization (phagocytosis or degradation), rendering the particles "unrecognizable" by the reticuloendothelial system. In addition, polymer micelles that range in size between about 10 nm and about 150 nm evade renal excretion and non-specific capture by the reticuloendo thelial system, and demonstrate prolonged circulation times in blood (see, e.g., Stolnik, S., et al., *Adv. Drug Deliv. Rev.* 16: 195-214 (1995); and Kataoka, K., et al. *J. Controlled Rel.* 24: 119-132 (1993)).

The nanoscale size of some polymer micelles facilitates "passive targeting," which results in significant accumulation of the micelles in tumor tissue, known as the EPR effect (again see Kwon, G. S. and Kataoka, K., *Adv. Drug Deliv. Rev.* 16: 295-309 (1995); and Kataoka, K., et al. *J. Controlled Rel.* 24: 119-132 (1993)). This EPR effect has been attributed to leaky tumor vessels that allow in particle extravasation in tumor sites, where there is no suchextravasation in normal tissues. Thus, EPR and lack of effective tumor lymphatic drainage prevent clearance of polymer micelles and promote accumulation of micelles in tumors (see Maeda, H., *Ad. Enzyme Regul.* 41: 189-207 (2001); and Duncan, R., *Pharm. Sci. Techn. Today* 2: 441-449 (1999)).

The aforementioned beneficial properties of polymer micelles can be successfully exploited for drug delivery, particularly in cancer as a tumor-specific delivery system. For example, in vivo studies have shown that the life span of animals and inhibition of tumor growth were increased considerably in mice treated with a drug incorporated in block copolymer micelle (see, e.g., Yokoyama, M., et al., *J. Controlled Release* 50: 79-92 (1998); and Kabanov, et al., W098/56334; and Kabanov et al., W098/56348)). Furthermore, recent studies have demonstrated that incorporation of antracyclines and other cytotoxic drugs in pluronic block copolymer micelles considerably can reduce drug resistance of various tumor cells (see Kabanov, A. V. and Lakhov, V., *Cr. Rev. Ther. Drug Targ.* 19: 1-73; and Kakizawa, Y., et al. *J. Am. Chem. Soc.* 121: 11247-11248 (1999)). Indeed, more than a 1000-fold increase in sensitivity of resistant tumors was observed for doxorubicin-loaded pluronic micelles (Alakhov, V., et al. *Colloids Surf., B: Biointerfaces* 16: 113-134 (1999)). A Phase II clinical trial of doxorubicin formulated with pluronic block polymer is currently being conducted (see Ranson, M., et al., The $5^{th}$ International Symposium on Polymer Therapeutics: From Laboratory to Clinical Practice, The Welsh School of Pharmacy, Cardiff University, Cardiff, UK, p. 15 (2002)). Together these studies suggest that incorporation of anticancer drugs in polymer micelles can increase the efficacy of cancer chemotherapy.

Factors that influence the performance of polymer micelles for drug delivery are loading capacity, release kinetics, circulation time, biodistribution, size, and stability (see, e.g., Allen, C., et al. *Colloids Surf., B: Biointerfaces* 16: 3-27 (1999)). Studies have shown that the in vivo anti-tumor activity of a drug is positively correlated with its in vitro stability. Therefore, a micelle structure with high stability is desired. One clear reason is that a delivery system is subject to severe dilution upon intravenous injection into an animal or human subject. In the bloodstream, under dilution, multimolecular micelles formed by block copolymers disintegrate or dissolve causing changes in their structure and size. Such instability of micelles is one concern for their application in vivo.

Formation of cross-links between the polymer chains of the core domain introduces covalent stabilization that reinforces micellar architecture and results in high stability against dilution and shear forces. The cross-linking results, in essence, in single molecules of nanoscale size. Therefore, in contrast to prior art supramolecular micelles, the nanoscale micelles of the present invention do not disintegrate under environmental variations such as dilution, changes in ionic strength or solvent system or pH.

There are several reports on the stabilization of the polymer micelles by cross-linking either within the core domain (see lijima, M., et al., *Macromolecules* 32: 1140-1146 (1999); Kim, J.-H., et al., *Polym. Adv. Technol.* 10: 647-654 (1999); Won, Y.-Y., et al., *Science* 283: 960-963 (1999); Guo, A., et al., *Macromolecules* 29: 2487-2493 (1996); Wooley, et al., U.S. Pat. No. 6,383,500; Kabanov, et al., U.S. Pat. No. 6,333,051; and Rapoport, N., *Colloids Surf., B: Biointerfaces* 16: 93-111 (1999)) or throughout the shell layer (Thurmond, K. B. II, et al., *Colloids Surf., B: Biointerfaces* 16: 45-54 (1999); Wooley, et al., U.S. Pat. No. 6,383,500; Zhang, Q., et al., *J. Am. Chem. Soc.* 122: 3642-3651 (2000); and Bütün, V., et al., *J. Am. Chem. Soc.* 121: 4288-4289 (1999)). In these cases, the cross-linked micelles maintained small size and core-shell morphology while their dissociation was suppressed. For example, stable nanospheres were prepared from poly(ethylene glycol)-b-polylactide micelles by using a polymerizable group at the core segment (again see lijima, M., et al., *Macromolecules* 32: 1140-1146 (1999)); which, in addition to stabilization against temperature change and time passage, obtained core polymerized micelles that exhibited excellent solubilization of rather large molecules such as taxol.

The incorporation of therapeutics or diagnostics (pharmaceutically active agents) into polymer micelles may be achieved through chemical and physical routes. Chemical routes generally involve covalent coupling of the drug to the hydrophobic block of the copolymer, leading to micelle-forming, polymer-drug conjugates (see, e.g., Kataoka, K., et al. *Adv. Drug Del. Rev.* 47: 113-131 (2001); Kataoka, K., et al., *J. Controlled Rel.* 24:119-132 (1993); Bader, H., et al., *Chem.* 123/124: 457-483; and Yokoama, M., et al., *Cancer Res.* 50: 1693-1700 (1990)). However, the physical encapsulation of drugs within the polymer micelle (also known as micellar nanocontainers) is generally a more attractive procedure and currently is being used for a wide variety of micellar systems because it is simpler and facilitates drug release (see Kabanov, A. V., et al., *FEBS Lett.* 258: 343-345 (1989); Hagan, S. A., et al., *Langmuir* 12: 2153-2163 (1996); and Kwon, G. S., et al. *Colloids Surf., B: Biointerfaces* 2: 429-434 (1994)).

The principles of the self-assembly of polymer micelles have been significantly advanced by using block and graft (linear polymers to which side chains have been "grafted") copolymers containing ionic and nonionic blocks. Upon interaction with oppositely charged polyions or surfactants, a special class of dispersed systems are formed, known as polymer complex micelles or block ionomer complexes, which combine the properties of polyelectrolyte complexes and block copolymer micelles (see, e.g., Harada, A. and Kataoka, K., *Macromolecules* 28: 5294-5299 (1995); Kabanov, A. V., et al., *Macromolecules* 29: 6797-6802 (1996); Bronich, T. K., et al., *Macromolecules* 30: 3519-3525 (1997); Bronich, T. K., et al., *Colloids Surf, B: Biointerfaces* 16: 243-251 (1999); and Harada, A., et al., *Macromolecules* 31: 288-294 (1998)). Micelles formed from block or graft copolymers are of interest because they allow the encapsulation of charged therapeutic molecules including proteins and nucleic acids. Moreover, polymer micelles entrapping plasmid DNA and oligonucleotides have been developed as non-viral DNA delivery systems (see Kabanov, A. V., et al., *Bioconjugate Chem.* 6: 639-643 (1995); Kataoka, K., et al., *Macromolecules* 29: 8556-8557 (1996); Katayose, S., et al., *Bioconjugate Chem.* 8: 702-707 (1997); Kabanov, A. V., et al., Self-Assembling Complexes for Gene Delivery: From Laboratory to Clinical Trial. John Wiley and Sons, Inc., New York (1998); Nguyen, H. K., et al., *Gene Ther.* 7: 126-138 (2000); Lemieux, P., et al., *J. Drug Target.* 8: 91-105 (2000); and Kikazawa, Y. and Kataoka, K., *Adv. Drug Deliv. Rev* 54: 203-222 (2002)).

The references discussed above demonstrate continuing efforts to provide polymeric means of carrying or delivering chemical agents such as pharmaceuticals. Thus, there is a need in the art for improved micelle formulations for drug delivery. The present invention satisfies this need in the art.

SUMMARY OF THE INVENTION

The present invention provides novel polymeric micelles for drug delivery having cross-linked, ionic cores; and methods of synthesis and uses therefor.

Accordingly, among its various aspects, the present invention provides a method for synthesizing an amphiphilic block polymer micelle comprising: forming block polymers having ionically-charged polymeric segments and nonionically-charged polymeric segments; neutralizing the ionically-charged polymeric segments with moieties of opposite charge under conditions that allow for self-assembly of polymer micelles; cross-linking the neutralized ionically-charged polymer segments with a cross-linking agent; and removing the moieties of opposite charge and unreacted cross-linking agent. In certain embodiments, the ionically-charged polymeric segment is polymethacrylic acid or polyacrylic acid and the non-ionically charged water soluble polymeric segment is poly(ethylene oxide). Also, in some embodiments, the moieties of opposite charge are metal ions or surfactants and the cross-linking agents are titrimetric cross-linking reagents. In addition, the methods of the present invention include incorporating a pharmaceutical or biological agent into the micelle.

In another aspect, the present invention also provides micelles synthesized by the aforementioned method. In one specific embodiment, the ionically-charged polymeric segment is polymethacrylic acid or polyacrylic acid, the non-ionically charged water soluble polymeric segment is poly(ethylene oxide), and the micelle further comprises cisplatin.

In yet a further aspect, the present invention also provides a method of delivering a pharmaceutically active agent to a cell, tissue (including, without limitation, cancerous tissue and/or tumors), or organ, comprising contacting the cell, tissue, or organ, in vivo or in vitro, with a composition containing an effective amount of micelles comprising amphiphilic copolymers having cross-linked ionic core domains and exterior shell domains, and further comprising a pharmaceutically-active agent. The pharmaceutically-active agent is contained within the cross-linked ionic core of the micelles. In these methods, the contact is for a period of time sufficient to introduce the pharmaceutically-active agent to the locus of the cell, tissue, or organ.

Further scope of the applicability of the present invention will become apparent from the detailed description provided below. However, it should be understood that the following detailed description and examples, while indicating preferred embodiments of the invention, are given by way of illustration only since various changes and modifications within the spirit and scope of the invention will become apparent from this detailed description to those skilled in the art.

BRIEF DESCRIPTION OF THE DRAWINGS

So that the manner in which the above recited features, advantages and objects of the present invention are attained and can be understood in detail, a more particular description of the invention, briefly summarized above, may be had by reference to the embodiments that are illustrated in the appended drawings. It is to be noted, however, that the appended drawings illustrate only certain embodiments of this invention and are therefore not to be considered limiting of its scope, for the present invention may admit to other equally effective embodiments.

DETAILED DESCRIPTION

In the following description, numerous specific details are set forth to provide a more thorough understanding of the present invention. However, it will be apparent to one of skill in the art that the present invention may be practiced without one or more of these specific details. In other instances, well-known features have not been described in order to avoid obscuring the present invention.

The specification describes the present invention primarily in terms of one embodiment, specifically, micelles containing cisplatin. However, the micelles and the methods of synthesis therefore of the present invention should not be limited to use with cisplatin. Indeed, any pharmaceutically active agent can be delivered using micelles according to the present invention.

The present invention provides micelles useful for the delivery of therapeutic agents comprising amphiphilic block copolymers where the micelles have cross-linked ionic core domains and exterior hydrophilic shell domains. In order to help the reader understand the following detailed description, the following definitions are provided:

The term "shell domain" means the outermost domain or peripheral layer of a micelle according to the present invention.

The term "interior core domain" means the domain of a micelle interior to the shell domain.

The term "amphiphilic copolymer" means a copolymer which contains at least one hydrophilic domain and at least one hydrophobic domain.

The term "block copolymer" means a combination of two or more chains of constitutionally or configurationally different features linked in a linear fashion.

The term "micelle" includes without limitation micelles having shapes of spheres, cylinders, discs, needles, cones, vesicles, globules, rods, ellipsoids, and any other shape that a micelle can assume under the conditions described herein, or any other shape that can be adopted through aggregation of the amphiphilic copolymers.

The term "cross-link" means a structure bonding two or more polymer chains together.

The term "pharmaceutically active agent" or "biologically active agent" means any physiologically or pharmacologically active substance that produces a local or systemic effect in animals including, without limitation, humans.

The term "mean particle diameter" means the average value of the various diameters of regularly- or irregularly-shaped particles.

Figure 1:
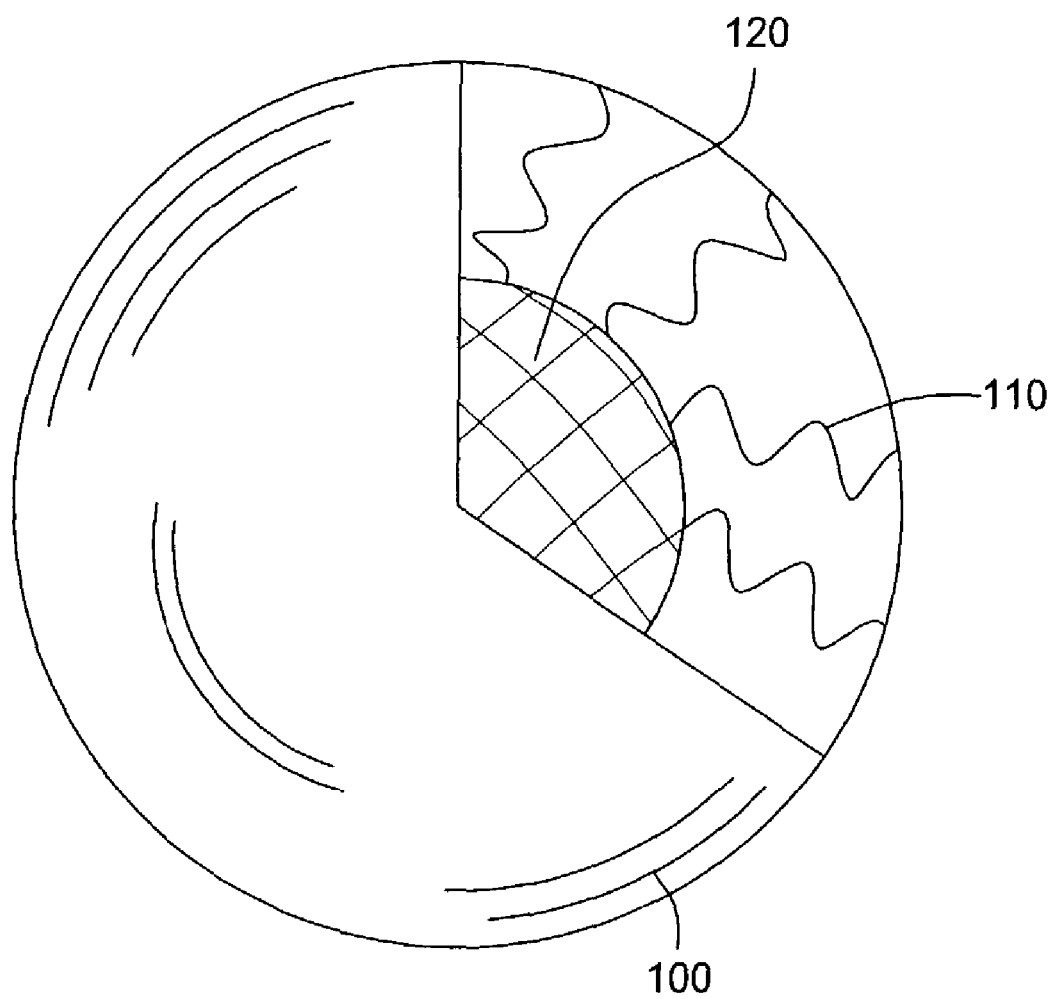
FIG. 1 is a cut-away representation of a micelle according to one embodiment of the present invention.

Thus, the present invention provides a novel type of polymer micelle and methods of synthesis therefor that combine several key structural components that are beneficial for effective drug delivery. These key structural components are a cross-linked ionic core, a hydrophilic PEO shell, and a nanoscale size. The unique combination of these three features in one polymer carrier improves the delivery of therapeutic and diagnostic agents. A polymer micelle according to the present invention has the structure shown in FIG. 1, representing hydrophilic nanospheres of core-shell morphology (seen at 100). The core of such a nanosphere is a network of cross-linked polyions (seen at 120), generally polyanions, that is surrounded by a shell of hydrophilic tethered chains (110). These cross-linked ionic polymer micelles have the following features:

the polyion core provides for effective binding to therapeutic and diagnostic agents, saccharides, proteins and nucleic acids via metal-complex formation;

cross-linking of the inner core prevents the micelle from degradation upon dilution;

the therapeutic and diagnostic agents, saccharides, proteins, nucleic acids and the like are protected from premature release and degradation in the core of the micelle;

hydrophilic tethered chains provide increased solubility and prevent interaction of blood plasma components with the micelles; and the nanoscale size avoids renal excretion but allows the micelles to invade sites with enhanced vascular permeability such as tumor tissue.

Figure 2:
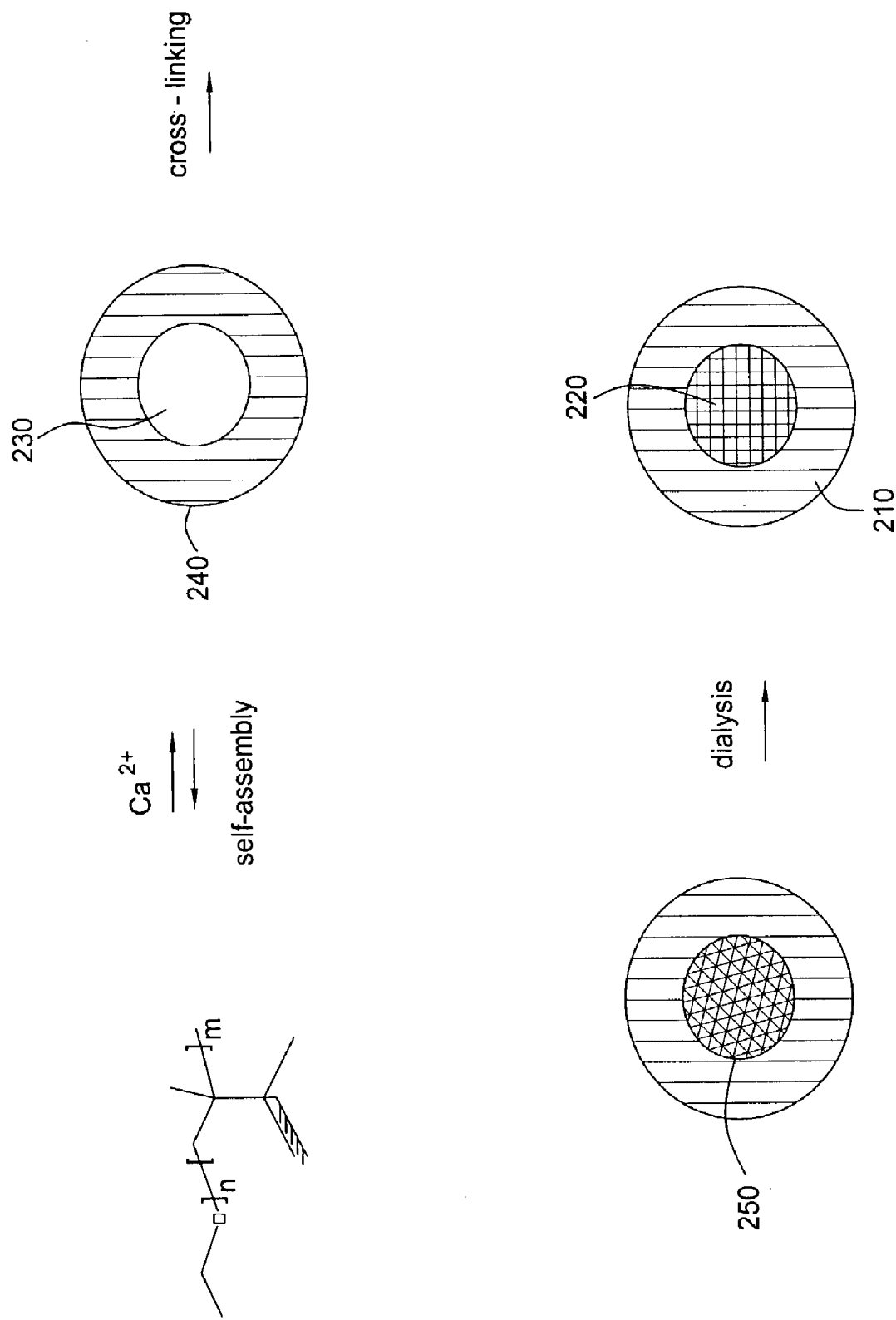
FIG. 2 demonstrates one embodiment of a process for synthesizing micelles according to the present invention.

FIG. 2 shows a general synthesis route for the micelles according to one embodiment of the present invention. The first step involves self-assembly of the amphiphilic block copolymers into polymer micelles in the presence of a changed moiety such as a metal ion or by a surfactant, here, $Ca^{+2}$. Electrostatic neutralization of the polyion block by the metal ions or the surfactant induces amphiphilicity and results in spontaneous micellization of the copolymer. The inner core of such micelles (seen at 230), thus, is composed of water-insoluble neutralized polyion chains surrounded by a shell of hydrophilic polymer chains (seen at 240). At a next step, cross-links throughout the core domain are formed via a reaction between the functional groups of the core polymer and an appropriate cross-linker (condensation, chain polymerization or addition reactions are all possible, depending on the nature of the ionic polymer and the cross-linking agent) to yield a cross-linked core (seen at 250), followed by extraction of the charged moiety via dialysis, chromatography or other method known in the art. As a result, polymer micelles with cross-linked ionic cores (220) and hydrophilic shells (210) are formed.

Polymer micelles with cross-linked ionic cores are highly unique, as nanscale hydrophilic polymer micelles cannot exist without the core cross-links. Moreover, the characteristics of the cross-linked polymer micelles can be controlled by changing the length of the polyionic and nonionic blocks of the initial copolymer, and/or by varying the degree of cross-linking and/or the type of the cross-linker in the core. Each of these polymer micelles represents a single nanostructured copolymer, so in extremely dilute conditions well below the critical micelle concentration for regular linear block copolymers, the polymer micelle of the present invention will not dissociate. Therefore, the present polymer system is resistant to the extremely dilute conditions occurring upon intravenous injection.

The cross-linked polymer micelle will interact with therapeutics or diagnostics such as, for example, cisplatin, and as a result, the charges of the anionic chains in the core of the cross-linked micelles will be neutralized and local contraction of the polyion segments will follow metal-complex formation. However, the complexed micelles will remain stable in aqueous dispersion due to the effect of hydrophilic exterior shell chains. The incorporation of therapeutic and diagnostic agents into the cross-linked core provides for strong drug retention in the carrier particles. Therefore, such agents are protected from the premature release and degradation. The copolymers of the present invention may be biodegradable or nonbiodegradable.

In the present invention, the ionically-charged polymeric segment may be selected from, without limitation, polymethylacrylic acid and its salts, polyacrylic acid and its salts, copolymers of acrylic acid and its salts, poly(phosphate), polyamino acids, polymalic acid, polylactic acid, aspartic acid, 1,4-phenylenediacrylic acid, ciraconic ackd, citraconic anhydride, trans-cinnamic acid, 4-hydroxy-3-methoxy cinnamic acid, p-hydroxy cinnamic acid, trans glutaconic acid, glutamic acid, itaconic acid, linoleic acid, linlenic acid, methacrylic acid, maleic acid, trans-β-hydromuconic acid, trans-trans muconic acid, oleic acid, vinylsulfonic acid, inyl phophonic acid, vinyl benzoic acid or vinyl glycolic acid.

When the ionically-charged polymeric segment of the present invention is a polyanionic segment, the non-ionically charged water soluble polymeric segment may be selected from, without limitation, polyetherglycols, poly (ethylene oxide), copolymers of ethylene oxide and propylene oxide, polysaccharides, polyvinyl alcohol, polyvinyl pyrrolidone, polyvinyltriazole, N-oxide of polyvinylpyridine, HPMA, polyortho esters, polyglycerols, or copolymers or derivatives thereof.

The neutralizing agents of the present invention are a moiety having a charge opposite that of the polyionic segment. Preferably, the neutralizing agent binds well and forms a complex with the polyionic segment, but also is easily removed by dialysis or other means known in the art and compatible with micelle chemistry.

One family of neutralizing agents are the mono-, di- and trivalent ions. For example, cations such as, but not limited to $Ca^{+2}$, $Mg^{+2}$, $Ba^{+2}$ or $Sr^{+2}$ are useful. Anionic neutralizing agents include, but are not limited to, $Cl^-$, $Br^-$, and the like.

Cationic surfactants are useful in the present invention to neutralize the charge of the ionically-charged polymeric segment when the polymeric segment is anionic. Such surfactants include single-, double- or triple-tailed surfactants, though single-tailed surfactants are preferred. Such surfactants suitable for use in present biological agent compositions include primary amines (e.g., hexylamine, heptylamine, octylamine, decylamine, undecylamine, dodecylamine, pentadecyl amine, hexadecyl amine, oleylamine, stearylamine, diaminopropane, diaminobutane, diaminopentane, diaminohexane, diaminoheptane, diaminooctane, diaminononane, diaminodecane, diaminododecane), secondary amines (e.g., N,N-distearylamine), tertiary amines (e.g., N,N',N'-polyoxyethylene(10)-N-tallow-1,3-diaminopropane), quaternary amine salts (e.g., dodecyltrimethylammonium bromide, hexadecyltrimethylammonium bromide, alkyltrimethylammonium bromide, tetradecyltrimethylammonium bromide, benzalkonium chloride, cetyldimethylethylammonium bromide, dimethyldioctadecyl ammonium bromide, methylbenzethonium chloride, decamethbnium chloride, methyl mixed trialkyl ammonium chloride, methyl trioctylammonium chloride), 1,2-diacyl-3-(trimethylammonio)propane (acyl group=dimyristoyl, dipalmitoyl, distearoyl, dioleoyl), 1,2-diacyl-3-(dimethylammonio)propane (acyl group=dimyristoyl, dipalmitoyl, distearoyl, dioleoyl), 1,2-dioleoyl-3-(4'-trimethylammonio) butanoyl-sn-glycerol, 1,2-dioleoyl-3-succinyl-sn-glycerol choline ester, cholesteryl (4'-trimethylammonio) butanoate), N-alkyl pyridinium and quinaldinium salts (e.g., cetylpyridinium halide, N-alkylpiperidinium salts, dialkyidimetylammonium salts, dicationic bolaform electrolytes ($C_{12}Me_6$; $C_{12}Bu_6$), dialkylglycetylphosphorylcholine, lysolecithin), cholesterol hemisuccinate choline ester, lipopolyamines (e.g., dioctadecylamidoglycylspermine (DOGS), dipalmitoyl phosphatidylethanolamidospermine (DPPES), N'-octadecylsperminecarboxamide hydroxytrifluoroacetate, N',N''-dioctadecylsperm inecarboxamide hydroxytrifluoroacetate, N'-nonafluoropentadecylosperminecarboxamide hydroxytrifluoroacetate, N',N''-dioctyl(sperminecarbonyl)glycinamide hydroxytrifluoroacetate, N'-(heptadecafluorodecyl)-N'-(nonafluoropentadecyl)-sperminecarbonyl)glycinamede hydroxytrifluoroacetate, N'-[3,6,9-trioxa-7-(2'-oxaeicos-11'-enyl )heptaeicos-18-enyl]sperminecarbox amide hydroxytrifluoroacetate, N'-(1,2-dioleoyl-sn-glycero-3-phosphoethanoyl)spermine carboxamide hydroxytrifluoroacetate), 2,3-dioleyloxy-N-[2(sperminecarboxamido)ethyl]-N,N-dimethyl-1-propanaminiu mtrifluoroacetate (DOSPA) (see, for example, Ciccarone et al., Focus 1993, 15:80), N,N',N'',N'''-tetramethyl-N,N',N'',N'''-tetrapalmitylspermine (TM-TPS), N-[1-(2,3-dioleyloxy)propyl]-N,N,N-trimethylamonium chloride (DOTMA), dimethyl dioctadecylammonium bromide (DDAB) (see, for example, Whitt et al., Focus 1991, 13:8), 1,2-dioleoyl-3-dimethyl-hydroxyethyl ammonium bromide (DORI), 1,2-dioleyloxypropyl-3-dimethyl-hydroxyethyl ammonium bromide (DORIE), 1,2-dioleyloxypropyl-3-dimethyl-hydroxypropyl ammonium bromide (DORIE-HP), 1,2-dioleyloxypropyl-3-dimethyl-hydroxybutyl ammonium bromide (DORIE-HB), 1,2-dioleyloxypropyl-3-dimethyl-hydroxypentyl ammonium bromide (DORIE-HPe), 1,2-dimyristyloxypropyl-3-dimethyl-hydroxyethyl ammonium bromide (DMRIE), 1,2-dipalmitoyloxypropyl-3-dimethyl-hydroxyethyl ammonium bromide (DPRIE), 1,2-distearoyloxypropyl-3-dimethyl-hydroxyethyl ammonium bromide (DSRIE), N,N-dimethyl-N-[2-(2-methyl-4-(1,1,3,3-tetramethylbutyl)-phenoxy]ethoxy) ethyl]-benzenemethanaminium, chloride (DEBDA), N-[1-(2,3-dioleyloxy)propyl]-N,N,N,-trimethylammonium methylsulfate (DOTAB), lipopoly-L(or D)-lysine, poly(L (or D)-lysine conjugated to N-glutarylphosphatidylethanolamine lysine, didodecyl glutamate ester with pendant amino group ($C_{12}GluPhC_nN^+$), ditetradecyl glutamate ester with pendant amino group ($C_{14}GluPhC_nN^+$), 9-(N',N''-dioctadecylglycinamido)acridine, ethyl 4-[[N-[3-bis(octadecylcarbamoyl)-2-oxapropylcarbonyl]glycinamido]pyrrole-2-carboxamido]-4-pyrrole-2-carboxylate, N',N'-dioctadecylornithylglycinamide hydroptrifluoroacetate, cationic derivatives of cholesterol (e.g., cholesteryl-3-β-oxysuccinamidoethylenetrimethylammonium salt, cholesteryl-3-β-oxysuccinamidoethylenedimethylamine, cholesteryl-3-β-carboxyamidoethylenetrimethylammonium salt, cholesteryl-3-β-carboxyamidoethylenedimethylamine, 3-β-[N-(N',N'-dimethylaminoetane-carbomoyl]cholesterol), pH-sensitive cationic lipids (e.g., 4-(2,3-bis-palmitoyloxy-propyl)-1-methyl-1H-imidazole, 4-(2,3-bis-oleoyloxy-propyl)-1-methyl-1H-imidazole, cholesterol-(3-imidazol-1-yl propyl)carbamate, 2,3-bis-palmitoyl-propyl-pyridin-4-yl-amine) and the like.

Suitable anionic surfactants to be usedin the present invention when the ionically-charged polymeric segment is cationic include alkyl sulfates, alkyl sulfonates, fatty acid soap including salts of saturated and unsaturated fatty acids and derivatives (e.g., arachidonic acid, 5,6-dehydroarachidonic acid, 20-hydroxyarachidonic acid, 20-trifluoro arachidonic acid, docosahexaenoic acid, docosapentaenoic acid, docosatrienoic acid, eicosadienoic acid, 7,7-dimethyl-5,8-eicosadienoic acid, 7,7-dimethyl-5,8-eicosadienoic acid, 8,11-eicosadiynoic acid, eicosapentaenoic acid, eicosatetraynoic acid, eicosatrienoic acid, eicosatriynoic acid, eladic acid, isolinoleic acid, linoelaidic acid, linoleic acid, linolenic acid, dihomo-gamma-linolenic acid, gamma-linolenic acid, 17-octadecynoic acid, oleic acid, phytanic acid, stearidonic acid, 2-octenoic acid, octanoic acid, nonanoic acid, decanoic acid, undecanoic acid, undecelenic acid, lauric acid, myristoleic acid, myristic acid, palmitic acid, palmitoleic acid, heptadecanoic acid, stearic acid, nonanedecanoic acid, heneicosanoic acid, docasanoic acid, tricosanoic acid, tetracosanoic acid, cis-15-tetracosenoic acid, hexacosanoic acid, heptacosanoic acid, octacosanoic acid, triocantanoic acid), salts of hydroxy-, hydroperoxy-, polyhydroxy-, epoxy- fatty acids, salts of carboxylic acids (e.g., valeric acid, trans-2,4-pentadienoic acid, hexanoic acid, trans-2-hexenoic acid, trans-3-hexenoic acid, 2,6-heptadienoic acid, 6-heptenoic acid, heptanoic acid, pimelic acid, suberic acid, sebacicic acid, azelaic acid, undecanedioic acid, decanedicarboxylic acid, undecanedicarboxylic acid, dodecanedicarboxylic acid, hexadecanedioic acid, docasenedioic acid, tetracosanedioic acid, agaricic acid, aleuritic acid, azafrin, bendazac, benfurodil hemisuccinate, benzylpenicillinic acid, p-(benzylsulfonamido)benzoic acid, biliverdine, bongkrekic acid, bumadizon, caffeic acid, calcium 2-ethylbutanoate, capobenic acid, carprofen, cefodizime, cefmenoxime, cefixime, cefazedone, cefatrizine, cefamandole, cefoperazone, ceforanide, cefotaxime, cefotetan, cefonicid, cefotiam, cefoxitin, cephamycins, cetiridine, cetraric acid, cetraxate, chaulmoorgic acid, chlorambucil, indomethacin, protoporphyrin IX, protizinic acid), prostanoic acid andits derivatives (e.g., prostaglandins), leukotrienes and lipoxines, alkyl phosphates, O-phosphates (e.g., benfotiamine), alkyl phosphonates, natural and synthetic lipids (e.g., dimethylallyl pyrophosphate ammonium salt, S-farnesylthioacetic acid, farnesyl pyrophosphate, 2-hydroxymyristic acid, 2-fluorpalmitic acid, inositoltrphosphates, geranyl pyrophosphate, geranygeranyl pyrophosphate, alpha-hydroxyfarnesyl phosphonic acid, isopentyl pyrophoshate, phosphatidylserines, cardiolipines, phosphatidic acid and derivatives, lysophosphatidic acids, sphingolipids and like), synthetic analogs of lipids such as sodium-dialkyl sulfosuccinate (e.g., Aerosol OT.RTM.), n-alkyl ethoxylated sulfates, n-alkyl monothiocarbonates, alkyl- and arylsulfates (asaprol, azosulfamide, p-(benzylsulfonamideo)benzoic acid, cefonicid, CHAPS), mono- and dialkyl dithiophosphates, N-alkanoyl-N-methylglucamine, perfluoroalcanoate, cholate and desoxycholate salts of bile acids, 4-chloroindoleacetic acid, cucurbic acid, jasmonic acid, 7-epi jasmonic acid, 12-oxo phytodienoic acid, traumatic acid, tuberonic acid, abscisic acid, acitertin, and the like.

In preparing micelles of the present invention, cross-linking the interior core domain can be achieved using a titrimetric cross-linking reagent. Preferably, the titrimetric cross-linking reagent is a bifunctional, trifunctional, or multifunctional cross-linking reagent. Any of the titrimetric cross-linking reagents shown in FIG. 3 can be usedin the methods of preparation of this invention. Cross-linking of the ionic core domain can be achieved by a variety of means including, but not limited to, condensation reactions, addition reactions, or chain polymerization reactions. Useful chain polymerization reactions include cationic chain polymerization, anionic chain polymerization, radical chain polymerization, and ring opening chain polymerization. Cross-linking can be achievedin a number of ways, including photochemically, spontaneously, by addition of a chain polymerization initiator, and by addition of titrimetric cross-linking reagents.

Titrimetric cross-linking reagents can have a variety of functional groups useful in reacting with functionalities on the amphiphilic copolymers. Such useful functional groups include nucleophilic groups, electrophilic groups, and groups which participate in pericyclic reactions.

Figure 3:
FIG. 3 shows the chemical formulas for one type of cross-linking agent useful in the present invention.
Figure 3:
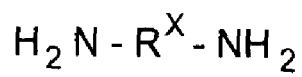
Figure 3:
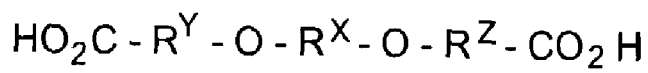
Figure 3:
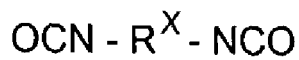
Figure 3:
Figure 3:
Figure 3:
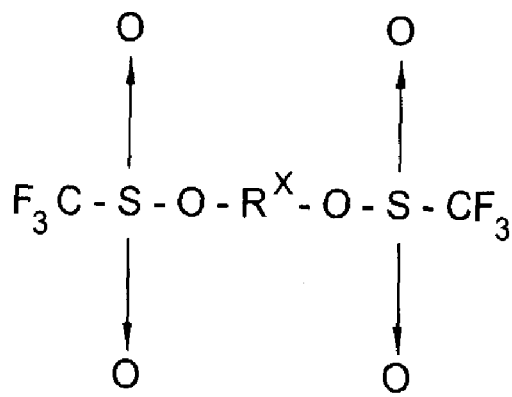
Figure 3:
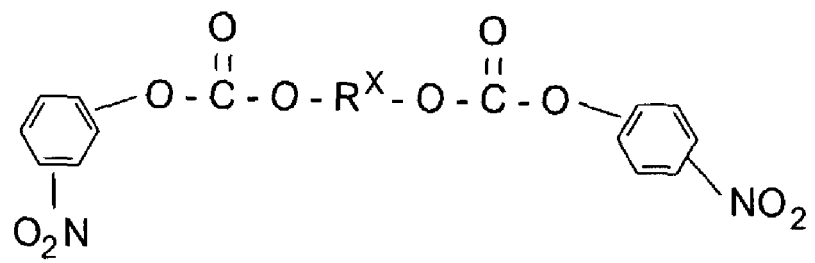

In FIG. 3, $R^x$, $R^y$, and $R^z$ can independently be alkanediyl, ether, polyether, polyoxyethylene, amine, polyalkyleneimine, polyethyleneimine, arene diyl, ester, polyester, amide, polyamide, carbonate, polycarbonate, saccharide, or polysaccharide, and X is a halogen.

Other titrimetric cross-linking. reagents can, for example, include multifunctional compounds such as polyols, polyamines, polyethyleneglycol multiarm stars, polycarboxylic acids, polycarboxylic acid halides, polyisocyanates, polymeric aromatic isocyanates, polyalkylhalides, polysulfonates, polysulfates, polyphosphonates, polyphosphates, alkyldiamines, alkanediols, ethanolamine, poly(oxyethylene), amino-substituted poly(oxyethylene), diamino-substituted poly(oxyethylene), poly(ethyleneimine), polyamino-substituted poly(oxyethylene), amino-substituted alcohols, substituted dendrimers, and substituted hyperbranched polymers.

The pharmaceutically or biologically active agents that can be usedin the present invention include, without limitation, inorganic and organic compounds, including drugs that act on cancerous tissues, tumors, the peripheral nerves, adrenergic receptors, cholinergic receptors, nervous system, skeletal muscles, cardiovascular system, smooth muscles, blood circulatory system, synaptic sites, neuroeffector junctional sites, endocrine system, hormone systems, immunological system, reproductive system, skeletal system, autatory of autocoid systems, alimentary and excretory systems, inhibitory of autocoids and histamine systems.

The active drugs that can be deliveredinclude anticonvulsants, analgesics, anti-inflammatories, calcium antagonists, anesthetics, antimicrobials, antimalarials, antiparasitics, antihypertensives, antihistamines, antipyretics, alpha-andrenergic agonist, alpha-blockers, anti-tumor compounds, biocides, bactericides, bronchial dilators, beta-andrenergic blocking drugs, contraceptives, cardiovascular drugs, calcium channel inhibitors, depressants, diagnostics, diuretics, electrolytes, hypnotics, hormonals, hyperglycemics, muscle contractants, muscle relaxants, opthalmics, psychic energizers, parasympathomimetics, saccharides, sedatives, sympathomimetics, tranquilizers, urinary tract drugs, vaginal drugs, vitamins, nonsteroidal anti-inflammatory drugs, angiotensin converting enzymes, polypeptides, proteins, and the like. Other beneficial pharmaceutically active agents known in the art that can be usedin conjunction with the micelles of the present invention are disclosedin Pharmaceutical Sciences, 14th Ed., edited by Remington, (1979) published by Mack Publishing Co., Easton Pa.; The Drug, The Nurse, The Patient, Including Current Drug Handbook, by Falconer, et al., (1974-1976) published by Saunders Company, Philadelphia, Pa.; Medicinal Chemistry, 3rd Ed., Vol. 1 and 2, by Burger, published by Wiley-Interscience, New York; Goodman & Gilman's The Pharmacological Basis of Therapeutics, 9th Ed., edited by Hardman, et al., (1996) published by McGraw-Hill, New York, N.Y.; andin Physicians' Desk Reference, 51st Ed., (1997) published by Medical Economics Co., Montvale, N.J.

One particularly useful therapeutic that may be usedin accordance with the present invention is cis-Dichlorodiaminoplatinum (II) (cisplatin, CDDP). Cisplatin is a well known metal complex that exhibits high antitumor activity andis widely usedin the treatment of testicular, ovarian, and head and neck tumors (for example, see Sherman, S. E. and Lippard, S. J., *Chem. Rev.* 87: 1153-1181 (1987)). Cisplatin especially is effective in combined drug therapy against squamous cell carcinoma, transitional cell carcinoma and small cell lung cancer (American Cancer Society textbook in Clinical Oncology (A. I. Holleb, D. J. Fink, and G. P. Murphy, Eds.), p. 691, American Cancer Society, Inc., Atlanta (1991)). However, the use of cisplatin clinically is limited due to its lower water solubility and significant toxic effects, in particular, acute and chronic nephrotoxicity (see Pinzani, V., et al., *Cancer Chemother. Pharmacol.* 35: 1-9 (1994)). Furthermore, the high glomerular clearance, of CDDP leads to an extremely short circulation periodin the blood (Siddik, Z. H., et al. *Biochem. Pharmacol.* 36: 1925-1932 (1987)).

Such problems, however, may be overcome by incorporating cisplatin into a carrier bearing carboxylic groups. It is known when the chloride ligands in CDDP are substituted with carboxylates, the newly-formed carboxylate ligands are still reversible due to their fairly low nucleophilicity, and are able to undergo an exchange reaction with chloride ions to regenerate cisplatin at physiological salt concentrations.

On the other hand, reduced solubility turnedinto an advantage upon designing a block copolymer micelle with a cisplatin-loaded core surrounded by a corona of hydrophilic tethered PEO chains. Indeed, simply mixing cisplatin with a PEO-poly(aspartic acid) (PEO-P(Asp)) block copolymer in distilled water led to spontaneous formation of stable micelles with diameters of about 20 nm at a critical substitution ratio of cisplatin to Asp units of 0.5 (Nishiyama, N., et al., *Langmuir* 15: 377-383 (1999)). Cisplatin-loaded micelles recently were confirmed to show longevity in blood circulation and notable tumor accumulation, achieving antitumor activity comparable to free cisplatin but with remarkably lower nephrotoxicity (Mizumara, Y., et al., *Jpn. J. Cancer Res.* 92: 328-326 (2001)). Thus, cisplatin-loaded micelles can provide a versatile tool for the purposeful modification of the pharmacokinetics and biodistribution of the drug, as well as for enhancing drug stability, decreasing side effects and enhancing drug targeting to selected tissues.

An issue in the drug delivery process is release kinetics. Drug release from polymer micelles depends primarily on the rate of diffusion of the drug from the micelles and micelle stability (see Allen, C., et al., *Colloids Surf., B: Biointerfaces* 16: 3-27 (1999)). Since the cross-linkedionic core micelles of the present invention are inherently stable, the diffusion-controlled release rate is controlled by the properties of cross-linkedionic core of the micelle (by, for example, the nature of cross-linking agent, the degree of cross-linking, and/or the composition of polyion-metal complex). However, the micelle must dissociate to release the entrapped drug at the targeted site. To this end, cross-linking by reversible, biodegradable, bonds is one embodiment of the present invention for achieving such release. For example, the bond may be cleavedin response to chemical stimuli given at the site of the drug action, such as by using cross-links containing cleavable disulfide bonds that are degradedin the presence of intracellular glutathione. An added advantage to this embodiment of the invention is that a degradable cross-linked core prevents long-term accumulation of the polymer micelles in the host. Thus biodegradation of the polymer micelle results in the degradation of the micelles, the product of which can be eventually removed through the renal clearance route.

Controlled drug release from the carrier also may be achieved by triggering changes in environmental parameters. For instance, certain tumors are characterized by low pH values, which could be exploited to induce structural transitions in the micelles resulting in drug release within the tumor. Similarly, acidification of the environment within endosomes can trigger drug release from micelles. For example, the charge density of polymethacrylic acid as a weak polyelectrolyte is strongly dependent on pH. Therefore, the stability of the polyion-metal complex in the core of micelles incorporating polymethacrylic acid will decrease when pH decreases due to the protonation of the carboxylic groups of the polyanion. As a result, such a polymer micelle structure is pH dependent. Furthermore, some drug resistant tumors have abnormally low cytoplasmic pH, which can enhance the effect of pH sensitive micelles in drug resistance.

In addition, in certain embodiments of the present invention, targeting entities may be included on the outer protions of the shell. Such targeting entities are used to "direct" the micelles to certain cells or tissues, or are used so that the micelles are "recognized" by certain cells or tissues. The targeting entities can be coupled to the micelles by various means, including linking with fuctional groups of the nonionic polymeric shell segments.

Thus, the present invention provides polymer micelles with cross-linked ionic cores as delivery vehicles for therapeutics, diagnostics, DNA (oligonucleotides and plasmids), RNA (including RNAi), proteins, and the like. The cross-linking of the ionic micelle core prevents the micelle from degradation upon dilution and protects the contained agents from premature release, decreasing any associated toxic side effects. In some embodiments, the bonds that provide the cross-linking are biodegradable. The present invention also provides methods of synthesis for such micelles, and methods of use therefor.

EXAMPLES

The block copolymers according to the present invention contain ionic and water-soluble nonionic polymeric segments. Block polymer complexes form spontaneously upon the mixing of the block ionomers with either oppositely charged surfactant molecules or polyions. Neutralization of the polyion charges leads to formation of hydrophobic domains, which tend to segregate in aqueous media, however, the water-soluble nonionic segments prevent complete aggregation and phase separation. As a result, the block polymer complexes of the present invention self-assemble into particles of nanoscale size and form stable aqueous dispersions. For example, the block polymer complexes formed between poly(ethylene oxide)-block-poly(sodium methacrylate) (PEO-b-PMA) and divalent metal cations were used for characterization and study. The block lengths were 210 and 227 repeat units for PEO and PMA respectively.

Example 1

Complex Formation of PEO-b-PMA with $Ca^{2+}$ ions

Mixing of an aqueous solution of poly(ethylene oxide)-block-poly(sodium methacrylate) (PEO-b-PMA) with a solution of $CaCl_2$ at molar ratio of $(Ca^{2+})/(COO^-)=6$ resultedin formation of slightly opalescent dispersions. Dynamic light scattering (DLS) measurements for the PEO-b-PMA/$Ca^{2+}$ mixtures revealed the formation of block copolymer-metal complex micelles with diameters approximately 130 nm. The low polydispersity index (<0.1) suggested a narrow particle size distribution. Spherical particles of core-shell morphology were observed by transmission electron microscopy (TEM) using uranyl acetate staining. The core of these micelles was composed of water-insoluble PMA chains neutralized by $Ca^{2+}$ ions and surrounded by a shell of PEO chains.

Example 2

Cross-Linking of the Core of the PEO-b-PMA/$Ca^{2+}$ Micelles

Cross-linking of the core of the micelles was achieved via condensation reactions between the carboxylic groups of PMA and the amine functional groups of 1,2-ethylenediamine in the presence of water-soluble carbodiimide. Briefly, an aqueous solution of 1-(3-dimethylaminopropyl)-3-ethylcarbodiimide hydrochloride (0.00275 mmole) was added dropwise in the solution of PEO-b-PMA/$Ca^{2+}$ micelles (0.1 mmole of methacrylic acid units). The mixture was stirred for approximately 10 minutes before the aqueous solution of the cross-linker, 1,2-ethylenediamine (0.0014 mmole), was added dropwise. The percentage of cross-linking was 25% and was based on the stoichiometric ratio of amine functional groups to carboxylic acid groups. The reaction mixture was allowed to stir overnight at room temperature. The size of PEO-b-PMA/$Ca^{2+}$ micelles in the dispersion slightly increased and was approximately 160 nm. This resulting size suggested that formation of cross-links was limited practically to intramicellar reactions.

The reaction mixture was then dialyzed against distilled water to remove $Ca^{2+}$ ions and byproducts of the cross-linking reactions. As a result of the cross-linking reaction, narrowly distributed particles with a net negative charge (zeta-potential, $\xi=-36$ mV) and diameter of about 220 nm were present in the aqueous dispersion. No changes in the size of the particles were detectedin the dispersion, even upon 100-fold dilution.

Example 3

Swelling Behavior of the Cross-Linked Micelles pH-induced dimensional changes of the cross-linked polymer micelles were studied by DLS and the results are presentedin Table 1. The size and net negative charge of the cross-linked micelles increased considerably with increasing pH. Such behavior is indicative of ionization and swelling of the network formed by cross-linked PMA chains that comprise the core of the micelle. This swelling is completely reversible; the protonation of carboxylic groups upon lowering of pH resultedin the collapse of micelle core and a decrease in the size of the particles. Therefore, ionic core of the cross-linked polymer micelle imparted a pH-sensitive hydrogel-like character to the micelles. Such an aspect of behavior is advantageous for the design of drug carriers with controlled loading and release characteristics.

TABLE 1

| PH | 6.2 | 7.7 | 8.5 | 8.8 |
|---|---|---|---|---|
| Diameter, nm | 217 | 240 | 300 | 308 |
| $\xi$-potential, mV | −36.3 | −44.4 | −45.1 | −48.2 |

Example 4

Incorporation of Cisplatin in Cross-Linked Polymer Micelles

Cisplatin was immobilizedin the cross-linked polymer micelles by a simple mixing procedure using an aqueous dispersion of polymer micelles at pH 9. Upon loading with cisplatin, the $\xi$-potential of the cross-linked polymer micelles increased from −52 mV to −27 mV indicating a decrease in the net negative charge. This indicates neutralization of the PMA segments due to the binding of cisplatin. Binding of cisplatin to the polymer micelles also led to the decrease in the circumference of particle size from about 320 nm to about 235 nm, which suggests contraction of the cross-linked PMA core of the micelle. The loaded polymer micelles were stable in aqueous dispersions, exhibiting no aggregation even after several days. Internal staining of the polymer micelles by virtue of the incorporated cisplatin allowed them to be visualized by transmission electron microscopy (TEM).

Example 5

Polymer Micelles with Polyion-Metal Complex Core

Block (or graft) copolymers containing anionic and non-ionic hydrophilic polymeric segments are used to prepare polyion complex micelles. For example, polymethacrylic acid (PMA) and polyacrylic acid (PAA) are used as anionic blocks. PEO is used as a hydrophilic block. The stability, size, and morphology of micelles strongly depends on the length of the anionic and hydrophilic chains. Therefore, copolymers of different architecture are tested. A series of PEO-b-PMA block copolymers with a PEO block constant length of 210 units and varying lengths of the anionic PMA block (30, 97, and 227 units) are used for analysis. PEO-b-PAA block copolymers are commercially available (Polymer Source Inc., Canada). The graft copolymers are synthesized by covalent attachment of monoamino-PEO (Sherwater Polymers, Inc.) to PAA of different lengths using carbodiimide as a coupling reagent (see, e.g., Hourdet, D., et al., *Polymer* 10: 2535-2547 (1997)).

Polymer micelles with polyion-metal complex cores are prepared by reacting block copolymers with $CaCl_2$ in aqueous solutions at different molar ratios of ($Ca^{2+}$)/($COO^-$). Generally, the binding affinity of metal ions affects the formation of the polyion complex, and the synthesis of micelles displaying small size (less than 100 nm) with high stability in the dispersion is preferred. Small micelle size is achieved by proper adjustment of the structure of the copolymers and the type of metal ions or surfactant used. $Ba^{2+}$ and $Sr^{2+}$ ions are two of the preferred metal ions used to prepare polymer micelles. The size, morphology, and stability of polymer micelles with polyion-metal complex cores may be characterized using DLS or TEM techniques known in the art. These experiments establish the relationship between the copolymer structure and the architecture of the assembled polymer micelles.

Example 6

Cross-Linking of the Micelle Core

Cross-links throughout the polyion-metal complex core of the polymer micelles of this example are formed via a condensation reaction between the carboxylic acid groups of the PMA or PAA and diamino cross-linking agents in the presence of 1-(3-dimetylaminopropyl)-3-ethylcarbodiimide hydrochloride in the aqueous media. Then byproducts of the cross-linking reaction and the metal ions, which have cross-linked the ionic core, are removed by exhaustive dialysis of the aqueous reaction mixtures against, e.g., water. The structure of the cross-linker selected and number of cross-links dictates the core composition and properties and can be adjusted as needed by one skilledin the art. Contributions of the hydrophobicity and length of the cross-linker in the structure and the swelling properties of the micelles of this example may be explored by using several diamino cross-linkers (1,2-ethylenediamine, hexamethylenediamine and/or 2,2'-(ethylenedioxy)bis(ethylamine)). The extent of cross-linking may be varied by addition of varying amounts of carbodiimide and cross-linker. Since density of cross-linking may compromise the loading capacity of the micelle, one skilledin the art should try several concentrations to achieve the properties required for the intended purpose and delivered therapeutic of the micelle. One objective of such studies may be to obtain stable micelles of small size with a minimal number of cross-links in the core. In addition, it may be of interest to include cleavable disulfide bonds into the micellar cross-linked core using, e.g., cystamine as a cross-linker. As a result of these experiments, a series of polymer micelles with cross-linkedionic cores of different composition are synthesized.

Example 7

Characterization of Polymer Micelle with Cross-Linked Ionic Core

The chemical composition of the polymer micelles of the present invention may be characterized by elemental analysis and FTIR, the apparent molecular weight of the micelles may be measured by size exclusion chromatography, and the concentration of carboxylate groups in cross-linked micelle may be determined by potentiometric titration. All such procedures are well known in the art.

The size (hydrodynamic diameter) and ξ-potential of the cross-linked micelles may be characterized, e.g., by DLS. Electrophoretic mobility measurements are performed using "ZetaPlus" Zeta Potential Analyzer (Brookhaven Instrument Co.) with a 50 mV solid state laser operating at a laser wavelength of 635 nm. The ξ-potential of the particles is calculated from the electrophoretic mobility values using software provided by manufacturer. The sizing measurements are performedin a thermostatic cell at a scattering angle of 90° using the same instrument equipped with the Multi-Angle Sizing Option (BI-MAS). To characterize the stability of the micelles in the dispersion, size measurements are repeated for several days with each sample.

The morphology of the polyion complex micelles is examined by transmission electron microscopy (TEM) using a negative staining technique. A drop of the sample solution is allowed to settle on a Formvar precoated grid for one minute. Excess sample is wicked away with filter paper and a drop of 1% uranyl acetate solution is allowed to contact the sample for one minute. The samples are studied using a Phillips 410 microscope.

DLS technique is used, generally, to characterize swelling behavior and stability of the cross-linked polymer micelles in the dispersion in response to changes in pH, concentration of low molecular mass electrolytes, and temperature. The effect of varying salt (NaCl) concentration is evaluatedin a series of size measurements at constant pH 7.4. Swelling transition, a process in which cross-linked micelles undergo upon changing the pH and/or salt concentration, may affect the loading and release characteristics of the micelles and such characteristics can be testedin this manner. Stability of the micelles in dispersion in the presence of bovine serum albumin also may be examined, to ensure that the micelles are preserved optimally in the presence of blood components such as serum proteins.

Degradation of the polymer micelles containing cleavable disulfide bonds in the cross-linked core is studied using a physiologically relevant reductive agent, such as glutathione. Polymer micelle dispersions are treated with various concentrations of glutathione (10 μM–1 mM) for 6, 12, and 24 hours at a physiological salt concentration (150 mM NaCl). Any change in the micelle structure through the cleavage of the disulfide bonds is studied by monitoring the change in the relative scattering light intensity, as a decrease in the molecular weight of the micelles is accompanied by a decrease in the scattering light intensity. These studies allow characterization of the extent to which cross-linked polymer micelles containing cleavable disulfide bonds in the core dissociate under reductive environment.

Example 8

Preparation of Cisplatin-Loaded Polymer Micelle

The aqueous dispersions of cross-linked micelles are mixed with an aqueous solution of an agent at an appropriate concentration (such as 1 mg/ml) and incubated for various periods of time (e.g., 24, 48, and 72 hours) at 37° C. The molar ratio of agent to functional groups of the core polymer of the micelle is variedin a range of, for example, from 0.25 to 5. In addition, the pH of the mixtures is variedin a range of, for example, from 6-9. Binding of agent to the polymer micelles is monitored by measuring the size and ξ-potential of the micelles. Unbound agent is removed by, for example, ultrafiltration using Centricon® Plus-20 centrifugal filter units (equipped with MWCO 100,000 membrane, Millipore), and the amount of the non-entrapped cisplatin in the filtrate can be determined using a Thermo Jarrell Ash Video 12 atomic absorption, spectrometer (AAS). Standard solutions are used for calibration.

For example, if the agent of interest is cisplatin, the platinum content in the cisplatin-loaded micelles may be determined using o-phenylenediamine as a ligand for Pt (II). For this purpose, aqueous dispersion of cisplatin-loaded micelles is mixed with o-phenylenediamine solution in DMF (1.2 mg/ml) at volume ratio of 1:1. The mixture is incubated at 100° C. for 10 minutes, and absorbance at 703 nm is measured using a Shimadzu UV-1601PC UV-VIS spectrophotometer. The amount of Pt (II) in the complexes is determinedin reference to standard solutions of free cisplatin. Using these data, the weight fraction of cisplatin in the micelle is determined. These studies allow identification of optimum time and concentration of cisplatin during incubation. The capacity of cross-linked micelles to bind cisplatin may be estimated for the polymer micelles of different structures. Specifically, the effect of cross-linking density in the core and structure of cross-linker on the cisplatin loading level is evaluated.

Example 9

Cisplatin Release Studies

If cisplatin is the agent being studied, it is known that cisplatin release from the cross-linked polymer micelles occurs at physiological conditions due to an inverse exchange reaction from the carboxylate group of PMA or PAA to the chloride ligand. Drug release kinetics may be investigatedin detail following a published procedure (see Peracchia, M. T., et al., *J. Controlled Release* 46: 223-231 (1997)). The cisplatin-loaded polymer micelle in phosphate buffered saline (PBS) (pH 7.4, 2.0 mL) is placedinto a dialysis bag (Spectra/Por-6, MWCO 1000) andimmediately immersedin 40 mL of PBS kept at 37° C. The concentration of cisplatin in the external solution is determined by AAS. From the release rate plot, kinetic information can be obtained. The release profiles are examined for cisplatin-loaded polymer micelles with different compositions of the core to address the effect of the micelle structure (degree of cross-linking, structure of cross-linker and copolymer). The changes in micelle size during the release studies are monitored using the aforementioned DLS technique. Generally, it has been observed that the sizes of the micelles increase after release of cisplatin. Such studies allow identifying cisplatin/ polymer micelle formulations for further evaluation using in vivo tumor models, and can be used for other therapeutic or diagnostic agents, proteins, nucleic acids and the like.

Example 10

Cell Lines for In Vitro Studies

Experiments to test cisplatin-delivered micelles are performed using the murine P388 leukemia cell line. This cell line has been used successfully in vitro and in vivo for evaluation of anticancer activity of cisplatin and other platinum complexes (see, e.g., Mirabelli, C. K., et al. *Cancer Res.* 48: 5447-5454 (1998)). Furthermore, it has been reported that subcutaneous implantation of P388 cells in the inguinal region produces solid tumors. The cell line is maintained in suspension in Roswell Park Memorial Institute (RPMI) 1640 media supplemented with 10% fetal bovine serum (FBS), penicillin and streptomycin (100 U/ml and 0.1 mg/ml, respectively), and 10 mM HEPES, at 37° C. in a humidified atmosphere with 5% $CO_2$.

Example 11

In Vitro Cytotoxicity Assay

The P388 cells are preincubated at 37° C. in 96-well plates at $2 \times 10^4$ cells/well and treated with various doses of: 1) the free cross-linked polymer micelle (to determine the toxicity of the micelle); 2) free drug; 3) the drug incorporated into the polymer micelle; and 4) the drug/polymer formulation with different micelle sizes. Plates are incubated for 24, 48, and 72 hours at 37° C. After treatment, cytotoxic effects are determined using a standard 3-(4.5-dimethylthiazol-2-yl)2.5-diphenyltetrazolium bromide (MTT) assay. Briefly, 25 μl of 5 mg/mL MTT in complete media containing 1 mM sodium pyruvate is added to each well. Following a 4-hour incubation of the plates at 37° C., the cells are solubilized by addition of 100 μl of assay solution (20% SDS in DMF-acetate buffer, pH 4.7, 1:2), and the absorbance; is measured at 450 nm with a BioRad microplate reader. These studies determine the $IC_{50}$ values (concentration of drug that caused a 50% reduction in absorbance) of free cisplatin and cisplatin incorporated in polymer micelles.

The use of in vitro cytotoxicity studies to characterize the polymeric micelles of the present invention is three-fold. First, these studies examine the toxicity of the cross-linked polymer micelles. It has been determined that PAA, PMA, and PEO have little if any toxicity (see, Uhrich, K. E., et al. *Chem. Rev.* 99: 3181-3198 (1999)). Second, the studies assess, e.g., the anticancer activity of the cisplatin incorporated into the cross-linked polymer micelles. In these studies, the $IC_{50}$ values of the free drug and the drug incorporated-into polymer micelle is determined from the dose-response curves. These data are used to finalize the dose regimens for in vivo studies. Third, the drug/polymer formulation with different micelle size/structure versus reactivity is determined and rationalized. The criteria for selecting one optimized formulation of an agent for animal studies include many factors. For example, in selecting a formulation for cisplatin, one may look for $IC_{50}$ values comparable or better than those of the free cisplatin. Even if the in vitro cytotoxic activity of the polymer micelle formulated drug is not changed compared to the free drug, one expects substantial benefit in using the polymer formulation in vivo, for example, due to EPR effect or decrease of drug toxicity.

Example 12

In Vitro Drug Resistance Studies

Also useful for the micelles of the present invention are studies to assess drug resistance, a serious problem encountered in any therapeutic regime. For example, to examine whether cisplatin incorporation in cross-linked polymer micelles might overcome drug resistance, cytotoxicity studies are conducted using A2780 and A2780cisR cell lines. Cells are seeded in 96-well plates at a density of 3000-4000 cells per well and left to adhere overnight. Serial dilutions of free cisplatin and cisplatin-loaded micelles are then added to wells. Cells are exposed to the drug for 24, 48, and 72 hours at 37° C., followed by washing with PBS, and maintained in the media for an additional 72 hours before the MTT assay. The cytotoxicity of the free and polymer micelle-formulated cisplatin are compared in each cell line. The resistance reversion indexes are determined as the ratio of $IC_{50}$ of the drug in the assay buffer to the $IC_{50}$ of the cisplatin incorporated into polymer micelle ($IC_{50,0}/IC_{50}$) to determine the extent of polymer affect on drug activity. Increase in the resistance reversion index for A2780cisR cells is indicative of overcoming drug resistance, which is an additional benefit for the use of the cross-linked micelle formulation.

Example 13

Animals

Female C57Bl/6 mice are obtained from Charles River Laboratories and used at 6 to 7 weeks of age. The animals are kept at 4-5 per cage with a filter cover under light (12 hour light/dark cycle, light on at 6 hours) and in a temperature (22°±1° C.) controlled environment. All manipulations with the animals are performed under a sterilized laminar hood. The animals have ad libitum access to irradiated food and sterile water.

Example 14

In Vivo Tumors

The murine P388 leukemia tumor model is used to evaluate the antitumor activities of cisplatin and cisplatin-loaded polymer micelles. Approximately $3 \times 10^6$ cells in 50 μl culture medium are implanted subcutaneously in the right inguinal region of the animals through a 1 to 2 cm long 22-guage needle. All procedures are done under sterile conditions. Tumors are allowed 8 days to become established and then animals with tumors from 0.09-0.1 $cm^2$ minimum size are selected, randomized and separated into treatment groups. Treatment groups contain 6-8 animals per group for statistical significance of results.

Example 15

Anticancer Effect In Vivo

While in vitro screening studies are a valuable tool for high throughput evaluations, to accurately examine the ability of a drug or drug combination, an in vivo model may be used to more closely mimic conditions realized in the clinic. For the study of the anticancer effect of cisplatin and cross-linked polymer micelle compositions in vivo, a solid P3888 leukemia tumor model is used. Each set of experiments is composed of the following treatment groups: 1)

saline control; 2) polymer micelles alone in saline; 3) cisplatin; and 4) cisplatin-loaded polymer micelles. The animals are treated with a single bolus intravenous administration of cisplatin or cisplatin-loaded polymer micelles in sterile saline solution (USP). The dosing regimens are finalized in accordance with the results of the in vitro cytotoxicity studies described supra.

Tumor volumes and animal body weight are measured on the day of treatment and twice weekly thereafter. The two largest perpendicular diameters of each tumor are measured with calipers and the tumor volume is estimated by the following formula: $TV=\frac{1}{2} \times L \times W^2$, where L and W are the length and width of the tumor, respectively. The tumor volume measured on the day of the treatment is taken as 100%. The results are expressed as a percentage of growth in relation to the volume of each tumor on the day of the treatment ($RV=V_i/V_o$, where $V_o$ is a mean tumor volume at the beginning of the treatment and $V_i$ is the mean tumor volume at any subsequent time). All animals are monitored daily for general health through the experiment. Animals are sacrificed in a $CO_2$ chamber if the tumor reaches a volume of greater than 1.5 $cm^3$ or measures greater than 1.5 cm in any direction; or if the tumor becomes ulcerated; or the animal exhibits body weight loss of greater than 20%. Drug efficacy is evaluated on day 14 using RV values for the treated group (T) and the control group (C): Growth inhibition (%)={1−RV (T)/RV (C)}×100.

The criteria for the efficacy of chemotherapy are as follows. Growth inhibition values from 58% to 89% are considered moderate activity, and ≧90% indicates good activity (see Goldin, A., et al. *Eur. J. Cancer* 17: 129-142 (1981)). Antitumor activity of cisplatin-loaded polymer micelles is compared to that of the cisplatin alone (as well as to the polymer micelle control). The toxicity of the free cisplatin and cisplatin formulated with polymer micelles during tumor therapy is assessed by measuring the body weight changes. Preference is given to formulations having higher antitumor activity and/or lower toxicity.

Earlier studies using cisplatin delivered by other polymer carriers indicated that anti-cancer activity of the cisplatin in the carrier might increase due to the passive targeting (EPR) effect. This could result in increased antitumor effect of the formulated drug as compared to the free drug. To further characterize that cisplatin-loaded polymer micelles as tumor-targetable drug delivery systems, the platinum accumulation in tumor, various tissues, and blood are assessed using AAS technique (see, e.g., Pera, M. F. and Harder, H. C., *Clin. Chem.* 23: 1245-1249 (1977); Fulco, R. A., et al., *Anticancer Res.* 10: 1603-1610 (1990); and Nashiyama, N., et al., *Pharm. Res.* 18: 1035-1041 (2001)). Specifically, tumor-bearing mice (six animals per group) are administered intravenously a single dose of cisplatin or cisplatin-loaded polymer micelles, and the animals are sacrificed after defined time periods (1, 4, 8, 24, 48, and 72 hours). Whole blood is collected in heparinized vials and immediately centrifuged at 12,000 rpm for 5 minutes to obtain plasma. The tumor, kidney, liver, spleen, and muscle will be excised, washed in ice-cold saline, and weighed. The plasma and each of the organs is decomposed by heating in nitric acid, evaporated and redissolved in 10 mM nitric acid to prepare samples for AAS measurements (see Fulco, R. A., et al., *Anticancer Res.* 10:1603-1610 (1990)). Platinum concentration and percent of dose in the plasma and organs are calculated. This experiment thus determines the amounts of cisplatin delivered into tumors as well as accumulated in other organs in the tumor bearing mice. Overall, these studies address the issue of delivering and maintaining sufficient concentrations of cisplatin at the site of action.

Example 16

Toxicology Study

Toxicity of the polymer micelle composition itself is an important consideration. Thus, toxicology studies are performed using cisplatin-loaded polymer micelles administered intravenously in mice. Initially, a brief dose-range finding study is performed for 7-days followed by a 28-day acute toxicity study. Second, comparative studies of the therapeutic doses of the cisplatin-loaded polymer micelle vs. free cisplatin are performed to identify potential pathologies resulting from the treatment. The highest dose not causing severe toxicity and two lower doses are used along with the cisplatin alone, the cross-linked polymer micelle alone, and a vehicle control. Five mice per group are treated. The measurements of the animal body weight, food and water consumption, as well as the blood analysis (blood chemistry panel and the hematology) are performed. Specifically, the determination of plasma creatinine and blood urea nitrogen levels, as well as histopathology studies of kidney tissue address the possible changes in renal function as a result of cisplatin treatment. The necropsy analysis at the end of 28 days characterizes weight of liver, spleen, kidney, lungs as well as tissue histology for potential pathologies.

While the present invention has been described with reference to specific embodiments, it should be understood by those skilled in the art that various changes may be made and equivalents may be substituted without departing from the true spirit and scope of the invention. In addition, many modifications may be made to adapt a particular situation, material, or process to the objective, spirit and scope of the present invention. All such modifications are intended to be within the scope of the invention.

All references cited herein are to aid in the understanding of the invention, and are incorporated in their entireties for all purposes.

The invention claimed is:

1. A method for synthesizing an amphiphilic block copolymer micelle comprising:
   forming block copolymers each having an ionically-charged polymeric segment and a nonioinically charged polymeric segment, wherein the ionically charged polymeric segment is a polyanionic form of polymethacrylic acid or polyacryilic acid and wherein the nonionically charged segment is poly(ethylene oxide)
   neutralizing the ionically-charged polymeric segment with moieties of opposite charge under conditions that allow for self assembly of polymer micelles, wherein the moieties of opposite charge are divalent or trivalent metals
   covalently cross-linking the neutralized ionically-charged polymer segments with a cross-linking agent
   removing the moieties of opposite charge and unreacted cross-linking agent
   replacing the moieties of opposite charge that were neutralizing the ionically charged polymeric segments with another charged agent after the removing step.

2. The method of claim 1, wherein the cross-linking agent reacts with the functional groups of the ionically-charged polymeric segments.

3. The method of claim 2, wherein about 0.5-80% of the functional groups are cross-linked.

4. The method of claim 3, wherein about 5-50% of the functional groups are cross-linked.

5. The method of claim 4, wherein about 10-40% of the functional groups are cross-linked.

6. The method of claim 5, wherein about 15-30% of the functional groups are cross-linked.

7. The method of claim 2, wherein the cross-linking agent is a titrimetric cross-linking reagent.

8. The method of claim 7, wherein the titrimetric compound is 1,2-ethylenediamine and the cross-linking is done in the presence of 1-(3-dimethylaminopropyl)-3-ethylcarbodiimide hydrochloride.

9. The of claim 1, wherein the cross-linking comprises a condensation reaction.

10. The method of claim 1, wherein the removing step is accomplished by dialysis, chromatography or ultrafiltration.

11. The method of claim 10, wherein the removing step is accomplished by dialysis.

12. The method of claim 1, wherein the another charged agent is a pharmaceutically active agent.

13. The method of claim 12, wherein the pharmaceutically active agent is an inorganic or organic compound.

14. The method of claim 13, wherein the inorganic or organic compound is a therapeutic that act on cancerous tissues, tumors, the peripheral nerves, adrenergic receptors, cholinergic receptors, nervous system, skeletal muscles, cardiovascular system, smooth muscles, blood circulatory system, synaptic sites, neuroeffector junctional sites, endocrine system, hormone systems, immunological system, reproductive system, skeletal system, autatory of autocoid systems, alimentary and excretory systems, inhibitory of autocoids or histamine systems.

15. The method of claim 14, wherein the therapeutic is an anticonvulsant, analgesic, anti-inflammatory, calcium antagonist, anesthetic, antimicrobial, antimalarial, antiparasitic, antihypertensive, antihistamine, antipyretic, alpha-andrenergic agonist, alpha-blocker, anti-tumor compound, biocide, bactericide, bronchial dilator, beta-andrenergic blocking drug, contraceptive, cardiovascular drug, calcium channel inhibitor, depressant, diagnostic, diuretic, electrolyte, hypnotic, hormone, hyperglycemic, muscle contractant, muscle relaxant, opthalmic, psychic energizers, parasympathomimetic, sedative, sympathomimetic, tranquilizer, urinary tract drug, vaginal drug, vitamin, nonsteroidal anti-inflammatory drug, angiotensin converting enzyme, or polypeptide.

16. The method of claim 15, wherein the pharmaceutically active agent is cisplatin.

17. The method of claim 12, wherein the incorporating step is accomplished by mixing.

18. The method of claim 17, wherein the pharmaceutically active agent is cisplatin, the cross-linking agent reacts with functional groups of the ionically-charged polymeric segments, and the mixing is in a molar ratio of cisplatin to functional group of about 0.1 to about 10.

19. The method of claim 18, wherein the mixing is in a molar ratio of cisplatin to functional group of about 0.5 to about 5.

20. The method of claim 13, wherein the inorganic or organic compound is a therapeutic that act on cancerous tissues, tumors, the peripheral nerves, adrenergic receptors, cholinergic receptors, nervous system, skeletal muscles, cardiovascular system, smooth muscles, blood circulatory system, synaptic sites, neuroeffector junctional sites, endocrine system, hormone systems, immunological system, reproductive system, skeletal system, autatory of autocoid systems, alimentary and excretory systems, inhibitory of autocoids or histamine systems.

21. The method of claim 20, wherein the therapeutic is an anticonvulsant, analgesic, anti-inflammatory, calcium antagonist, anesthetic, antimicrobial, antimalarial, antiparasitic, antihypertensive, antihistamine, antipyretic, alpha-andrenergic agonist, alpha-blocker, anti-tumor compound, biocide, bactericide, bronchial dilator, beta-andrenergic blocking drug, contraceptive, cardiovascular drug, calcium channel inhibitor, depressant, diagnostic, diuretic, electrolyte, hypnotic, hormone, hyperglycemic, muscle contractant, muscle relaxant, opthalmic, psychic energizers, parasympathomimetic, sedative, sympathomimetic, tranquilizer, urinary tract drug, vaginal drug, vitamin, nonsteroidal anti-inflammatory drug, angiotensin converting enzyme, or polypeptide.

22. The method of claim 21, wherein the pharmaceutically active agent is cisplatin.

23. A method for synthesizing an amphiphilic block copolymer micelle comprising:
   forming block copolymers having ionically-charged polymeric segment and nonionically charged polymeric segment, wherein the ionically-charged polymeric segment is a polyanionic form of polymethacrylic acid or polyacryilic acid and wherein the nonionically charged segment is poly(ethylene oxide)
   neutralizing the ionically-charged polymeric segments with moieties of opposite charge under conditions that allow for self assembly of polymer micelles, wherein the moieties of opposite charge are divalent or trivalent metals
   covalently cross-linking the neutralized ionically-charged polymer segments with a cross-linking agent by a condensation reaction.
   removing the moieties of opposite charge and unreacted cross-linking agent
   replacing the moieties of opposite charge that were neutralizing the ionically charged polymeric segments with another charged agent after the removing step.

24. The method of claim 23, wherein the cross-linking group is a titrimetric cross-linking reagent.

25. The method of claim 24, wherein the titrimetric compound is 1,2-ethylenediamine and the cross-linking is done in the presence of 1-(3-dimethylaminopropyl)-3-ethylcarbodiimide hydrochloride.

26. The method claim 23, further comprising the step of incorporating a pharmaceutically acceptable agent into the cross-linked ionic core after the removing step.

27. The method of claim 26, wherein the pharmaceutically active agent is cisplatin.

* * * * *

UNITED STATES PATENT AND TRADEMARK OFFICE
CERTIFICATE OF CORRECTION

PATENT NO. : 7,332,527 B2
APPLICATION NO. : 10/440221
DATED : February 19, 2008
INVENTOR(S) : Bronich et al.

It is certified that error appears in the above-identified patent and that said Letters Patent is hereby corrected as shown below:

Column 8, Line 36, please delete "usedin" and insert --used in--;

Column 9, Line 33, please delete "usedin" and insert --used in--;

Column 9, Line 41, please delete "achievedin" and insert --achieved in--;

Column 10, Line 2, please delete "usedin" and insert --used in--;

Column 10, Line 12, please delete "delieveredinclude" and insert --delivered include--;

Column 10, Line 27, please delete "usedin" and insert --used in--;

Column 10, Line 28, please delete "disclosedin" and insert --disclosed in--;

Column 10, Line 40, please delete "usedin" and insert --used in--;

Column 10, Line 43, please delete "andis" and insert --and is--;

Column 10, Line 44, please delete "usedin" and insert --used in--;

Column 10, Line 57, please delete "periodin" and insert --period in--;

Column 11, Line 1, please delete "turnedinto" and insert --turned into--;

Column 11, Line 23, please delete "cross-linkedionic" and insert --cross-linked ionic--;

Column 11, Line 26, please delete "cross-linkedionic" and insert --cross-linked ionic--;

Column 11, Line 33, please delete "cleavedin" and insert --cleaved in--;

Column 11, Line 36, please delete "degradedin" and insert --degraded in--;

Column 13, Line 15, please delete "detectedin" and insert --detected in--;

Column 13, Line 25, please delete "presentedin" and insert --presented in--;

Column 13, Line 31, please delete "resultedin" and insert --resulted in--;

Column 13, Line 51, please delete "immobilizedin" and insert --immobilized in--;

UNITED STATES PATENT AND TRADEMARK OFFICE
CERTIFICATE OF CORRECTION

| | | |
|---|---|---|
| PATENT NO. | : 7,332,527 B2 | |
| APPLICATION NO. | : 10/440221 | |
| DATED | : February 19, 2008 | |
| INVENTOR(S) | : Bronich et al. | |

It is certified that error appears in the above-identified patent and that said Letters Patent is hereby corrected as shown below:

Column 14, Line 55, please delete "skilledin" and insert --skilled in--;

Column 14, Line 64, please delete "skilledin" and insert --skilled in--;

Column 15, Line 5, please delete "cross-linkedionic" and insert --cross-linked ionic--;

Column 15, Line 28, please delete "performedin" and insert --performed in--;

Column 15, Line 46, please delete "evaluatedin" and insert --evaluated in--;

Column 15, Line 51, please delete "testedin" and insert --tested in--;

Column 16, Line 13, please delete "variedin" and insert --varied in--;

Column 16, Line 14, please delete "variedin" and insert --varied in--;

Column 16, Line 33, please delete "determinedin" and insert --determined in--;

Column 16, Line 52, please delete "investigatedin" and insert --investigated in--;

Column 16, Line 55, please delete "placedinto" and insert --placed into--;

Column 16, Line 56, please delete "andimmediately" and insert --and immediately--;

Column 17, Line 11, please delete "andin" and insert --and in--;

Column 17, Line 17, please delete "maintainedin" and insert --maintained in--;

Column 17, Line 44, please delete "incorporatedin" and insert --incorporated in--;

Column 17, Lines 52-53, please delete "incorporatedinto" and insert --incorporated into--;

Column 18, Line 11, please delete "seededin" and insert --seeded in--;

Column 18, Line 15, please delete "maintainedin" and insert --maintained in--;

UNITED STATES PATENT AND TRADEMARK OFFICE
CERTIFICATE OF CORRECTION

PATENT NO. : 7,332,527 B2
APPLICATION NO. : 10/440221
DATED : February 19, 2008
INVENTOR(S) : Bronich et al.

It is certified that error appears in the above-identified patent and that said Letters Patent is hereby corrected as shown below:

Column 18, Line 18, please delete "comparedin" and insert --compared in--;

Column 18, Lines 20-21, please delete "incorporatedinto" and insert --incorporated into--;

Column 18, Line 34, please delete "andin" and insert --and in--;

Column 18, Line 52, please delete "separatedinto" and insert --separated into--;

Column 18, Line 63, please delete "realizedin" and insert --realized in--;

Column 19, Line 6, please delete "finalizedin" and insert --finalized in--;

Column 19, Line 21, please delete "sacrificedin" and insert --sacrificed in--;

Column 19, Lines 52-53, please delete "administeredintravenously" and insert --administered intravenously--;

Column 19, Line 56, please delete "bloodis" and insert --blood is--; please delete "collectedin" and insert --collected in--; please delete "andimmediately" and insert --and immediately--;

Column 19, Line 59, please delete "washedin" and insert --washed in--;

Column 19, Line 61, please delete "redissolvedin" and insert --redissolved in--;

Column 19, Line 66, please delete "accumulatedin" and insert --accumulated in--;

UNITED STATES PATENT AND TRADEMARK OFFICE
CERTIFICATE OF CORRECTION

PATENT NO.        : 7,332,527 B2
APPLICATION NO.   : 10/440221
DATED             : February 19, 2008
INVENTOR(S)       : Bronich et al.

It is certified that error appears in the above-identified patent and that said Letters Patent is hereby corrected as shown below:

Column 20, Lines 10-11, please delete "administeredintravenously" and insert --administered intravenously--;

Column 20, Line 31, please delete "skilledin" and insert --skilled in--;

Column 20, Line 38, please delete "aidin" and insert --aid in--;

Column 20, Line 39, please delete "incorporatedin" and insert --incorporated in--.

Signed and Sealed this

Fifteenth Day of July, 2008

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,332,527 B2 | Page 1 of 1 |
| APPLICATION NO. | : 10/440221 | |
| DATED | : February 19, 2008 | |
| INVENTOR(S) | : Tatiana K. Bronich et al. | |

It is certified that error appears in the above-identified patent and that said Letters Patent is hereby corrected as shown below:

Column 1, line 6
  Please insert --under grant No. 0071682 awarded by the National Science Foundation--
  after the word "support".

Signed and Sealed this
Sixth Day of December, 2011

David J. Kappos
*Director of the United States Patent and Trademark Office*